US011813143B2

(12) United States Patent
Leung et al.

(10) Patent No.: US 11,813,143 B2
(45) Date of Patent: Nov. 14, 2023

(54) TISSUE CARE DEVICES INCLUDING MICROSTRUCTURES

(71) Applicant: KitoTech Medical, Inc., Seattle, WA (US)

(72) Inventors: Cheuk Yin Paul Leung, Bellevue, WA (US); Ron Berenson, Mercer Island, WA (US)

(73) Assignee: KitoTech Medical, Inc., Seattle, WA (US)

( * ) Notice: Subject to any disclaimer, the term of this patent is extended or adjusted under 35 U.S.C. 154(b) by 914 days.

(21) Appl. No.: 16/589,912

(22) Filed: Oct. 1, 2019

(65) Prior Publication Data

US 2020/0100943 A1   Apr. 2, 2020

Related U.S. Application Data

(60) Provisional application No. 62/786,726, filed on Dec. 31, 2018, provisional application No. 62/739,704, filed on Oct. 1, 2018.

(51) Int. Cl.
*A61F 13/00* (2006.01)
*A61L 27/36* (2006.01)
*A61L 27/52* (2006.01)

(52) U.S. Cl.
CPC .. *A61F 13/00021* (2013.01); *A61F 13/00017* (2013.01); *A61F 13/00038* (2013.01);
(Continued)

(58) Field of Classification Search
USPC ......................................................... 606/214
See application file for complete search history.

(56) References Cited

U.S. PATENT DOCUMENTS

| 4,430,998 A * | 2/1984 | Harvey | A61B 17/085 606/216 |
| 5,497,933 A * | 3/1996 | DeFonzo | A61B 17/0684 227/176.1 |

(Continued)

FOREIGN PATENT DOCUMENTS

| CN | 113556983 | 10/2021 | |
| FR | 2844445 A1 * | 3/2004 | A61B 17/0642 |

(Continued)

OTHER PUBLICATIONS

SMTL Dressings Datacard http://www.dressings.org/Dressings/mepitel.html (Year: 2009).*

(Continued)

*Primary Examiner* — Kim M Lewis
(74) *Attorney, Agent, or Firm* — Schwegman Lundberg & Woessner, P.A.

(57) ABSTRACT

A wound cover device can include a backing, a micro-structure device, and one or more of a wound dressing and a skin replacement layer. The backing can be stretchable. The micro-structure device can include a plurality of fasteners, such as micro-staples, micro-pins, micro-barbs and the like, that can be used to attach the wound cover device to tissue such as skin. The micro-structure device can be stretchable to stretch with the backing. The micro-structure device can be configured such that the fasteners are positioned in a two-dimensional pattern or fill-in an interior portion of the wound dressing or skin replacement layer. The fasteners of the micro-structure device can extend through the wound dressing or skin replacement layer. The micro-structure device can additionally be placed around a perimeter or edge region of the backing.

28 Claims, 7 Drawing Sheets

(52) U.S. Cl.
CPC ........ *A61F 13/00063* (2013.01); *A61L 27/36* (2013.01); *A61L 27/52* (2013.01); *A61F 2013/00157* (2013.01)

(56) References Cited

U.S. PATENT DOCUMENTS

| | | | | |
|---|---|---|---|---|
| 5,738,474 | A | * 4/1998 | Blewett | A61B 17/07207 411/920 |
| 6,566,577 | B1 | * 5/2003 | Addison | A61F 13/0203 602/56 |
| 2009/0226424 | A1 | 9/2009 | Hsu | |
| 2011/0034953 | A1 | * 2/2011 | Milo | A61B 17/0644 606/213 |
| 2012/0245629 | A1 | * 9/2012 | Gross | A61B 17/06 606/228 |
| 2014/0046348 | A1 | 2/2014 | Soltanian | |
| 2017/0128273 | A1 | * 5/2017 | Smith | A61F 13/0276 |

FOREIGN PATENT DOCUMENTS

| | | | | |
|---|---|---|---|---|
| GB | 2527617 A | * 12/2015 | ....... | A61F 13/00008 |
| IN | 202117019954 | 1/2022 | | |
| JP | 2003533326 A | 11/2003 | | |
| JP | 2011518017 A | 6/2011 | | |
| JP | 5212039 B2 | 3/2013 | | |
| JP | 2014516605 A | 7/2014 | | |
| JP | 2015523139 A | 8/2015 | | |
| JP | 2022508612 | 1/2022 | | |
| WO | WO-9308776 A1 | * 5/1993 | ............. | A61L 27/34 |
| WO | 0189392 | 11/2001 | | |
| WO | 2011112888 | 9/2011 | | |
| WO | 2013188884 | 12/2013 | | |
| WO | 2014046348 | 3/2014 | | |
| WO | 2014121051 | 8/2014 | | |
| WO | 2017151806 | 9/2017 | | |

OTHER PUBLICATIONS

Mepitel One, Wound Source https://web.archive.org/web/20160701025849/https://www.woundsource.com/product/mepitel-one (Year: 2016).*
Mount Sinai.Org., Skin Graft,2017 https://www.mountsinai.org/health-library/surgery/skin-graft#:~:text=The%20graft%20is%20carefully%20spread,for%203%20to%205%20days. (Year: 2017).*
Yanagisawa et al., Stapling technique through transparent gauze dressing to fix skin grafts, Nov. 29, 2017,Shinshu University School of Medicine, Plastic and Reconstructive Surgery, 3-1-1, Asahi, Matsumoto 390-8621 https://www.sciencedirect.com/science/article/pii/S2468912217300561 (Year: 2017).*
WO 9308776 A1 (Year: 1993).*
GB 2527617 a (Year: 2015).*
"International Application Serial No. PCT US2019 054105, International Preliminary Report on Patentability dated Apr. 15, 2021", 8 pages.
"International Application Serial No. PCT US2019 054105, International Search Report dated Feb. 12, 2020", 5 pages.
"International Application Serial No. PCT US2019 054105, Written Opinion dated Feb. 12, 2020", 6 pages.
"Chinese Application Serial No. 201980079562.0, Voluntary Amendment Filed Feb. 16, 2022", with English claims, 9 pages.
"European Application Serial No. 19791016.9, Response Filed Feb. 1, 2022 to Communication Pursuant to Rules 161(1) and 162 EPC dated Jul. 29, 2021", 10 pages.
"Japanese Application Serial No. 2021-543974, Notification of Reasons for Refusal dated Jun. 23, 2023", w/ English Translation, 8 pgs.

* cited by examiner

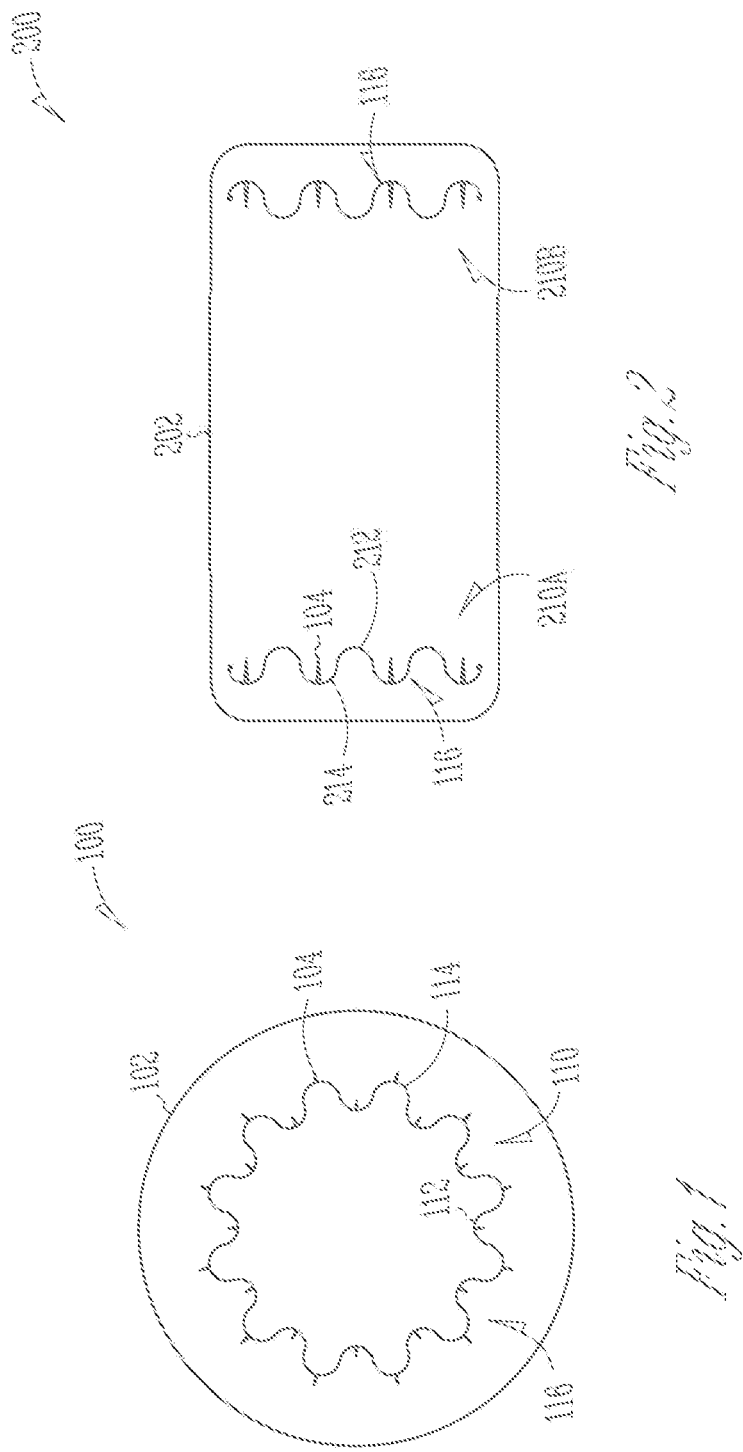

TISSUE CARE DEVICES INCLUDING MICROSTRUCTURES

CLAIM OF PRIORITY

This application claims the benefit of U.S. Provisional Patent Application Ser. No. 62/739,704, filed on Oct. 1, 2018, and U.S. Provisional Patent Application Ser. No. 62/786,726, filed on Dec. 31, 2018, the benefits of priority of which are claimed hereby, and which are incorporated by reference herein in their entirety.

TECHNICAL FIELD

The present disclosure pertains generally, but not by way of limitation, to devices and methods for tissue care. More specifically, but not by way of limitation, the present disclosure relates to devices and methods for fixation, attachment, security and stabilization of wound covers, wound dressings, skin substitutes, skin grafts and the like.

BACKGROUND

There are nearly 7 million patients in the United States with chronic wounds, including those due to burns, traumatic injuries, life threatening skin diseases, pressure ulcers, diabetic ulcers, and venous and arterial ulcers. Many of these patients are elderly and disabled, and chronic wounds represent a significant burden for them. Quality of life for these patients can be diminished due to the wounds limiting mobility, drainage of wounds, and foul odor. In addition, limited mobility of the patients puts them at risk for other medical problems, including pneumonia, additional chronic ulcers, venous thrombosis, and other conditions. These patients are also at significant risk of serious and life-threatening infections and gangrene from the wound itself which, in an extreme case, can result in the need to amputate extremities. In addition, many patients require long-term care lasting several months. Others require frequent and prolonged hospitalizations for wound care, resulting in significant costs and poor quality of life. Total healthcare costs for chronic wounds amount to over $50 billion per year, around the time of the filing of the present application.

Acute wounds, such as burns, wounds, such as scrapes and punctures, and surgical wounds are also common. There are over 700,000 patients with serious burns of which 100,000 require intensive treatment, according to statistics around the time of the filing of the present application. Traumatic injuries due to motor vehicle accidents and other causes are responsible for large numbers of wounds each year. Another source of acute wounds is those due to surgery. Finally, many patients suffer from life-threatening skin diseases that develop serious skin wounds.

Chronic wounds close slowly and incompletely in the majority of patients. Treatments can include wound dressings, the WoundVac or other vacuum assist devices also referred to as negative pressure dressings, electrical stimulation, skin substitutes (also referred to as artificial skin), skin grafts (allograft, xenograft, or autograft), and hyperbaric oxygen. Dressings are most commonly used and applied directly to the wound. Dressings are used to cover the wound to protect it from damage and further injury, prevent infection, absorb fluids, and maintain a moist environment that is optimal for healing. Dressings can also incorporate anti microbial agents, hemostatic agents, or wound healing materials that promote the heating of wounds. For acute wounds, dressings are the primary therapy although skin substitutes and skin grafts are sometimes necessary. For burns, skin substitutes, skin grafts, dressings and sometimes hyperbaric oxygen are all used.

OVERVIEW

The dislodgement of dressings from the skin is a challenging problem. The dressings are typically affixed to the skin with adhesive that is incorporated into the dressing or via an adhesive bandage. The adhesive weakly adheres to the skin making it at risk of dislodging from the skin. Additionally, when the adhesive becomes wet, it can also fall off of the skin, because adhesive does not adhere in a moist environment. Since wounds often ooze fluid, this is an especially common problem.

In addition, the skin of patients with skin ulcers is often fragile related to their advanced age and underlying conditions such as diabetes, venous insufficiency, or arterial insufficiency. Consequently, their skin is prone to damage due to the adherence of the adhesives and adhesive tapes. This can occur while they are applied to, worn on, or removed from the skin. This can result in additional ulcers and place the patients at risk for more infections.

Dislodgement of dressings from the skin has a material impact on the wound healing process and increases risk of infections. Loss of the protective covering of a wound dressing and its absorbent properties as well as other therapeutic agents that can be incorporated into the dressing has significant clinical consequences for patients. These include further direct damage from outside objects, increased pain, risk of infections, bleeding, disfigurement, incomplete, delayed, or non-healing of the skin wounds, and in severe circumstances, gangrene.

Skin substitutes are also used to protect skin hut also contain materials that promote wound healing. Skin grafts are used to replace severely damaged and necrotic skin. These materials are often attached with sutures or staples placed around the perimeter of the graft or skin substitute. This is suboptimal because the rest of the graft is not attached to underlying tissue. It is subject to motion, especially lateral shear, which can prevent interaction with underlying tissue. This can reduce the wound healing effects of skin substitutes and the engraftment of skin grafts.

Replacement of skin substitutes, skin grafts, and dressings can also lead to pain for patients when additional procedures are needed to replace these materials. In addition to clinical issues, there are significant added costs when dressings, skin substitutes, or skin grafts fall off prematurely or fail in patients. Dressings can cost more than $20 and up to several hundred dollars each. They are commonly applied several times per week and thus costs can be significant if the dressings need to be replaced more frequently. Skin substitutes often cost thousands of dollars, while skin grafting surgical procedures cost several thousand dollars.

Skin substitutes are used to either promote engraftment of skin, serve as a substitute for skin, or promote ingrowth and regeneration of the patient's own skin. Skin grafts are used to replace damaged or necrotic skin. Skin substitutes and skin grafts are typically attached to the patient's skin by using sutures, staples, adhesive bandages or some combination of these products They are usually attached around the outer portions of the skin graft or skin substitutes, which is suboptimal. This is because skin substitutes and skin grafts have additional issues related to motion and shear that affect their efficacy, which are described above.

The present inventors have recognized that, in order for skin substitutes and skin grafts to be effective, the entire surface, or nearly the entire surface (such as at a plurality of points distributed over the entire surface), of the product should remain stable and in contact with the underlying patient's tissue, thereby minimizing any local shear movements between skin substitute or skin grafts and the wound surface or tissue. Although sutures, staples, and adhesive bandages can provide some degree of attachment to the skin, they are suboptimal. This is because they only secure the outside perimeter of skin substitutes and natural skin to the underlying tissue. This leaves the vast majority of the skin substitutes and natural skin unattached to underlying tissue. Given that these materials are subject to movement and shear, this puts them at risk of detachment and also reduces their ability to promote wound healing. In addition, underlying tissues generate exudate, which can also lead to detachment of skin substitutes and skin grafts. The exudate can also contain molecules that inhibit wound healing. To help overcome this, the skin graft is often subjected to a process of meshing prior to application, which provides apertures to promote drainage, however, this is not used for skin substitutes. Other problems with using sutures and staples are that they can be damaging to the patient's skin and can cause bleeding, infection, pain, and disfigurement. In addition, they can be challenging to apply to the fragile skin of patients with chronic skin ulcers. For example, the skin tends to tear when sutures are tightened and consequently, the suture is no longer able to be securely anchored to the skin or wound. In the rare cases where they are used to attach the inner portion of skin grafts and skin substitutes, they are also challenging to apply due the fragility of these materials. Adhesive bandages used to attach skin substitutes and skin grafts to patient's tissues such as skin, suffer from the same problems listed above for wound dressings.

Products that generate a vacuum, known as vacuum assist devices, are an effective method of promoting wound healing. They consist of a piece of a device that generates a vacuum, which is attached to tubing that is attached to the wound. Typically, adhesive is used to attach the wound vacuum tubing to the skin surrounding the wound. The adhesive can cause skin irritation and damage, and also become dislodged, rendering the treatment ineffective. There is also a need to attach the sponge-like material to the underlying tissue that separates it from the vacuum. Adhesive ordinarily cannot be used for this purpose due to the moist tissue of the wound.

The present disclosure provides devices that solve these problems related to wound covers and dressings, including their wound healing, anti-microbial, and hemostatic properties, and skin substitutes and skin grafts. Most importantly, the present disclosure provides secure anchoring of dressings, skin substitutes, and skin grafts and covers to the skin. Devices of the present disclosure utilize tiny microstructures, such as micro-staples, rather than adhesives. This provides superior attachment to the underlying tissue thus providing improved healing and reducing costs associated with replacing dressings, skin substitutes, and skin grafts that dislodge from the skin. In addition, the microstructures are less damaging to the skin to which they are attached, such as around the periphery of wounds, and thus there is less risk of additional damage that occurs with adhesive bandages, sutures, and staples. Furthermore, the ability of microstructures to be used in fragile materials, including skin substitutes and some types of dressings and skin grafts, is also important to allow the secure attachment and provide optimal healing. Microstructures can be incorporated into skin grafts and skin substitutes, and thus be used to secure the attachment not only around the perimeter but throughout the wound or underlying tissue, such as at a plurality of points distributed over the entire surface. This provides better interaction with underlying tissue and thus promotes wound healing and skin regeneration. The microstructures can also be used to provide multiple apertures throughout skin substitutes, dressings, and skin grafts to enhance drainage which reduces risk of detachment and also removes molecules that can inhibit wound healing. These apertures also allow oxygen to enter the wound to promote wound healing. These apertures also allow excess exudate to drain preventing tension that can lead to dislodgement of these materials from the wound area or skin. Furthermore, the apertures allow space for the skin to grow and thus cover the wound with healthy tissue.

Wound vacuum assisted closure (VAC) devices typically need to be attached to the skin and adhesive materials suffer from the limitations in these devices as in wound dressings. Additionally, a non-adhesive material typically must be placed between the sponge and the VAC to prevent disruption of the graft when removing the dressing. As an alternative, microstructures could be used to attach the dressing eliminating the need for the non-adhesive material.

The spring characteristics of the microstructure arrays provide important features to improve the effectiveness of the technology. The wound and surrounding tissue move with skin motion. In addition, wounds are subject to edema, which results in swelling of the tissue. This can result in shear between the wound, underlying tissues and patient skin and the wound dressings, skin substitutes, and skin grafts. Shear can lead to tissue damage, inflammation, and infection, incomplete engraftment of skin grafts, and the suboptimal interaction of skin substitutes with the wound. The springs in the microstructure arrays enable the device to stretch, expand, and contract, and thus reduce shear and enable more consistent and uniform contact between the wound and underlying tissue and the wound dressings, skin substitutes, and skin grafts. This reduces irritation, inflammation, scarring, and infection. In addition, the springs also reduce the risk of the wound dressing, skin substitute, or skin graft detaching from the skin, wound, or underlying tissue.

EXAMPLES

The present disclosure provides devices and methods for securely covering a wound by attaching a wound dressing, skin substitute, and/or skin grafts to the skin, wound or underlying tissue.

In some examples, the present disclosure provides a microstructure wound cover comprising one or more microstructures for attaching the cover to a tissue (e.g., patient's skin). The one or more microstructures can effectively allow the microstructure wound cover to be attached to a tissue. The tissue can be skin, wound, or underlying tissue.

In some examples, the present disclosure provides a wound dressing comprising one or more microstructures for attaching the wound dressing to a tissue (e.g., patient's skin). The one or more microstructures can effectively allow the microstructure wound cover to be attached to a tissue by insertion of the microstructures into tissues, and thereby provide mechanical anchoring. The tissue can be skin, wound, or underlying tissue.

In some examples, the present disclosure provides a microstructure for attaching skin substitutes to a tissue (e.g., patient's skin). The one or more microstructures can effectively allow the microstructure wound cover to be attached to a tissue. The tissue can be patient skin wound, or underlying tissue. The patient can be a person or animal.

In some examples, the present disclosure provides a microstructure for attaching a skin graft to a tissue (e.g., patient's skin, wound, or underlying tissue). The one or more microstructures can effectively allow the microstructure wound cover to be attached to a tissue. The tissue can be patient skin, wound, or underlying tissue. The patient can be a person or animal.

In some examples, the present disclosure provides a microstructure for attaching a wound vacuum device to a tissue (e.g., patient's skin). The one or more microstructures can effectively allow the microstructure wound cover to be attached to a tissue. The tissue can be patient skin, wound, or underlying tissue. The patient can be a person or animal.

The present disclosure provides microstructure arrays for attaching skin graft, skin substitutes, a wound dressing or wound cover to a tissue (e.g., skin, wound, or underlying tissue) or a combination thereof. In some examples, the wound dressing or wound cover comprises one or more microstructure arrays. In some examples, the array comprises a plurality of microstructure portions, each of the plurality of microstructure portions comprising at least one microstructure for securing the array to the tissue, and at least one of the plurality of microstructure portions can comprise at least one structure with spring characteristics. Spring characteristics can exist in one or multiple directions and can be in directions along the plane of the dressing or cover. The one or more microstructures can allow the microstructure wound cover to be attached to a tissue. The tissue can be patient's skin; wound, or underlying tissue.

The wound dressings, skin substitutes, skin grafts or wound covers disclosed herein can be attached over or incorporated into a wound for one or more of the purposes of protecting the wound from infection or physical damage, promoting wound healing, providing hemostasis, medical device attachment thereto for monitoring wound conditions, acting as a platform to facilitate drug delivery, or promoting engraftment of a skin graft.

In one example, the present disclosure provides a method for attaching a wound dressing, skin substitute, skin graft, or wound cover onto a tissue of a subject, the method comprising, attaching one or more wound dressing, skin substitute, skin graft, wound cover or a combination of one or more of these materials onto a tissue of a subject, wherein the wound dressing, skin substitutes, skin graft, or wound cover comprises at least one microstructure for securing the array to the tissue. The skin substitutes, skin graft or wound cover disclosed herein can or can not include adhesives, furthermore, the microstructure technology disclosed herein can be utilized in both single-use, e.g., disposable, and multi-use, e.g., reusable, medical devices for wound management.

In one example, the present disclosure provides a method for attaching skin substitutes onto a tissue of a subject, the method comprising, attaching one or more wound dressings or wound covers onto a tissue of a subject, the wound dressing or wound cover having a body of skin substitutes, wherein the wound dressing or the wound cover comprises at least one microstructure for securing the array to the tissue.

The microstructures are used to attach the body of the wound dressing, or tire skin replacement layer, such as a skin product, skin substitute or skin graft, to the patient's skin or wound tissue itself. For attachment to the cover, dressing, skin substitute or skin graft, adhesives, sutures, thread, staples, or tapes can be used to attach the microstructure array to the microstructure-based material. The microstructures can be adhered, sewn, attached or otherwise coupled to the body of the dressing, cover, or skin product.

In one example, the present disclosure provides a kit comprising one or more wound covers and/or one or more wound dressings and one or more wound closure devices disclosed herein. In some examples, such a kit comprises a plurality of wound closure devices and one or more wound covers and/or wound dressings which can comprise skin substitutes or include skin grafts.

In one example, the present disclosure provides a kit comprising one or more microstructure wound cover and/or one or more microstructure wound dressing and optionally one or more wound closure device disclosed herein. The wound cover or wound dressing body can comprise skin substitutes or donor skin.

It should be appreciated that all combinations of the foregoing concepts and additional concepts discussed in greater detail below (provided such concepts are not mutually inconsistent) are contemplated as being part of the inventive subject matter disclosed herein, and any of the examples provided herein can be combined with one another (provided such combination is not mutually inconsistent). In particular, all combinations of claimed subject matter appearing at the end of this disclosure are contemplated as being part of the inventive subject matter disclosed herein. It should also be appreciated that terminology explicitly employed herein that also can appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

INCORPORATION BY REFERENCE

All publications, patents, and patent applications mentioned in this specification are herein incorporated by reference to the same extent as if each individual publication, patent, or patent application was specifically and individually indicated to be incorporated by reference. U.S. patent application Ser. No. 14/408,244 (which published as Pub. No. US 2015/0305739 ["the '739 Publication"]), filed Jun. 17, 2013, and U.S. patent application Ser. No. 15/446,999 (which published as Pub. No. US 2017/0333039 ["the '039 Publication"]), filed Mar. 1, 2017, are incorporated herein by reference, in their entirety.

BRIEF DESCRIPTION OF THE DRAWINGS

Some of the novel features of the invention are set forth with particularity in the appended claims. A better understanding of the features and advantages of the present invention will be obtained by reference to the following detailed description that sets forth illustrative examples, in which the principles of the invention are utilized, and the accompanying drawings.

FIG. 1 illustrates a wound cover with microstructures, in accordance with one or more examples herein.

FIG. 2 illustrates a wound dressing with microstructures, in accordance with one or more examples herein.

DETAILED DESCRIPTION

Figure 3:
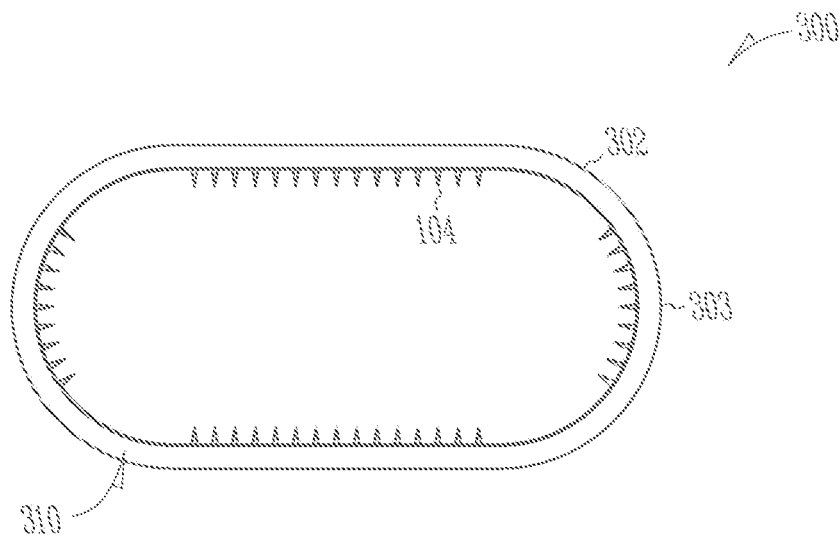
FIG. 3 illustrates a wound cover or dressing with microstructures, in accordance with one or more examples herein.

A better understanding of the features and advantages of the present disclosure will be obtained by reference to the following detailed description that sets forth illustrative examples, in which the principles of examples of the present disclosure are utilized, and the accompanying drawings.

Although the detailed description contains many specifics, these should not be construed as limiting the scope of the disclosure but merely as illustrating different examples and aspects of the present disclosure. It should be appreciated that the scope of the disclosure includes other examples not discussed in detail above. Various other modifications, changes and variations which will be apparent to those skilled in the art can be made in the arrangement, operation and details of the methods, systems, and apparatus of the present disclosure presided herein without departing from the spirit and scope of the invention as described herein.

FIG. 1 shows a non-limiting example of a wound cover disclosed herein. FIG. 1 shows a circular wound cover 100. The wound cover 100 includes a main body 102 that is circular shaped. The wound cover also includes a microstructure array 110 of microstructures 104. The microstructures can be coupled or otherwise attached to the body 102 of the wound cover 100. The microstructures engage a tissue or other object to couple the cover to the object. As described further below, the microstructures can additionally be used to hold skin replacement layers, such as skin substitutes (also referred to as artificial skin), or skin grafts (allograft, xenograft, or autograft), on a wound in the tissue.

As shown in FIG. 1, the microstructure array is a continuous, circular array that includes a plurality of spring portions 116. In additional examples, the microstructure array can comprise a plurality of circular arc segments located around a common center. Spring portions 116 can comprise shaped elongate members, such as wires, bars, fibers and the like, and can be made of metals and plastics. As shown in FIG. 1, the spring portions 116 are curved, e.g., undulating portions, and provide for flexibility and movement of the microstructures 104 of the array with respect to each other. The microstructures can be of any form that engages with tissue or an object, such as those discussed in the '739 and '039 Publications. The spring portions can be of any form, such as those discussed in the '739 and '039 Publications.

As further shown in FIG. 1, the microstructure array can include a staggered arrangement of microstructures. For example, the array can include inner microstructures 112 located more towards the center of the body 102 of the cover 100 and outer microstructures 114 located more towards the outer perimeter of the body 102 of the cover 100.

FIG. 2 shows a rectangular wound dressing 200 comprising microstructures 104 for attachment to a tissue or other object. The microstructures are shown in two arrays 210A, 201B, each on longitudinally opposite ends of the dressing, but could also be included on more than two sides, e.g., all 4 sides of the cover or dressing. Also, other shapes, e.g., pentagonal, hexagonal, oval, jagged, curved, etc., are contemplated, and microstructures could be on one or more of each additional side of the device.

As shown in FIG. 2, each array 210 comprises a plurality of spring portions 116. The spring portions 116 are curved and provide for flexibility and movement of the microstructures 104 of the arrays 210A, 210B with respect to each other. The microstructures can be of any form that engages with tissue or an object, such as those discussed in the '739 and '039 Publications. The spring portions can be of any form, such as those discussed in the '739 and '039 Publications.

The microstructures are shown in linear arrays 210A, 210B of a single row, however, each microstructure array can include a staggered arrangement of microstructures. For example, the array can include inner microstructures located at inner portions 212 of the array, such that they are in a location more towards the center of the body 202 of the cover 200 and outer microstructures 214 located more towards the ends of the body 202 of the cover 200.

Skin grafts are used to replace damaged or necrotic skin. The grafts are derived from the patient (autologous), a human donor (allograft), or animal source (xenograft). When possible, the skin can be meshed to provide apertures to enable drainage of exudate and improve oxygenation of the underlying tissue. Meshing also enables expansion of the donor tissue thus improving growth. Meshing can result in a poor cosmetic appearance upon healing of the graft. To attach the graft to the underlying tissue, sutures and staples are placed around the perimeter of the graft. The surrounding skin is often fragile making it challenging to secure the graft with sutures or staples. In addition, placing these devices around the perimeter does not secure the inner portion of the graft subjecting it to shear and the potential for fluid to build up underneath the graft. This can lead to poor engraftment or complete detachment of the donor graft. The devices of the present disclosure are configured to improve upon conventional skin grafting techniques and alleviate some or all of the drawbacks or deficiencies associated therewith described herein.

The prevention of shearing forces that can disrupt graft take is accomplished by securing the graft, to the site, which typically involves use of a bolster dressing or a negative pressure dressing. A bolster dressing typically is composed of moistened cotton balls wrapped in a petroleum gauze such as Xeroform, which is secured by placing sutures radially around the wound and tying them to each other over the bolster dressing to provide constant, light pressure to the graft. For skin grafts to the lower extremity, an Unna boot, dressing can be applied, as it performs the necessary action of maintaining graft integrity but also allows for early mobilization. However, both of these approaches can fail leading to graft failure.

Alternatively, negative pressure dressings (vacuum-assisted closure [VAC]) can promote wound healing. They prevent shearing forces and reduce fluid collection between the graft and recipient bed, thereby facilitating plasmatic imbibition and revascularization, leading to a significant improvement in overall split-thickness skin graft survival. A nonadherent material typically must be placed as an interface between the skin graft and the VAC sponge to prevent disruption of the graft when removing the dressing.

Traditional wound dressing products including gauze, lint, plasters, bandages (natural or synthetic), and cotton wool are dry and used as primary or secondary dressings for protecting the wound from microbial contamination. Gauze dressings made out of woven and non-woven fibers of cotton, rayon, and polyesters afford some sort of protection against bacterial infection. Bandages made out of natural cotton wool and cellulose or synthetic bandages made out of polyamide materials. Generally, traditional dressings are indicated for the clean and dry wounds with mild exudate levels or used as secondary dressings. Since traditional dressings fail to provide moist environment to the wound they have been replaced by modern dressings with more advanced formulations. Traditional wound dressing products described herein can be attached using the microstructures described herein.

Modern wound dressing have been developed to facilitate the function of the wound rather than just to cover it. These dressings are focused to keep the wound from dehydration and promote healing. Semi-permeable wound dressings are composed of transparent and adherent polyurethane which permits transmission of water vapor, $O_2$ and $CO_2$ from the wound. It also provides autolytic debridement of eschar and is impermeable to bacteria. Initially, films were made from nylon derivatives with an adhesive polyethylene frames as the support which made them occlusive. Examples include Opsite™, Tegaderm™, Bioocclusive™. Hydrogel wound dressings are insoluble hydrophilic materials made from synthetic polymers such as poly (methacrylates) and polyvinyl pyrrolidine. The high water content of hydrogels (70-90%) helps granulation tissues and epithelium in a moist environment. Some examples of hydrogels are Intrasite™, Nu-gel™, Aquaform™ polymers, sheet dressings, impregnated gauze, and water-based gels. Hydrocolloid dressings are among the most widely used interactive dressings and are consist of two layers, inner colloidal layer and outer water-impermeable layer. These dressings are made up of the combination of gel forming agents (carboxymethylcellulose, gelatin and pectin) with other materials such as elastomers and adhesives. Hydrocolloids are permeable to water vapor but impermeable to bacteria and also have the properties of debridement and absorb wound exudates. Granuflex™, Comfeel™, Tegasorb™ are examples and available in the form of sheets or thin films. Alginate dressings are made from the sodium and calcium salts comprising mannuronic and guluronic acid units. Absorbent and biodegradable alginates are derived from seaweed. Absorption capability is achieved by strong hydrophilic gel formation, which limits wound exudates and minimizes bacterial contamination. Sorbsan™, Kaltostat™, Algisite™ are some alginate dressings that are commercially available.

Bioactive wound dressings are produced from biomaterials that play an important role in the healing process. These dressings are known for their biocompatibility, biodegradability and non-toxic nature and are derived generally from natural tissues or artificial sources, such as collagen, hyaluronic acid, chitosan, alginate and elastin. Polymers of these materials are used alone or in combination depending on the nature and type of wound. Biological dressings are sometimes incorporated with growth factors and antimicrobials to enhance wound healing process. Modern wound dressing products described herein, such as semi-permeable wound dressings, hydrogels and hydrocolloids, can be attached using the microstructures described herein.

Medicated dressings incorporating drugs play an important role in the healing process directly or indirectly by removal of necrotic tissues. Some commonly incorporated compounds include antimicrobial agents, growth factors, and enzymes. Commercially available antimicrobial dressings include Cutisorb™. Silver impregnated dressings available are Fibrous hydrocolloid, Polyurethane foam film and silicone gels. Examples of silver impregnated dressings include Acticoat and Actisorb Antiseptic Iodine dressing is another anti-microbial dressing. Medicated dressing products described herein can be attached using the microstructures described herein.

Composite dressings are versatile and convenient for both partial and full thickness wounds. A composite or combination dressing has multiple layers and each layer is physiologically distinct. Most of the composite dressings possess three layers. Composite dressings can also include an adhesive border of non-woven fabric tape or transparent film Composite wound dressing products described herein can be attached using the microstructures described herein.

Electrical stimulation is also used to promote wound healing in which a power source is attached to electrodes that are attached to the skin. Recently, what are referred to as nanogenerators are incorporated into bandages or dressings to generate the electric field. Wound dressings incorporating nanogenerators can be attached using the microstructures described herein.

Topical approaches are also used to directly generate oxygen into the wound itself to promote wound healing. In some cases, the oxygen is generated in materials consisting of wound dressings.

Skin substitutes or artificial skin substitutes are derived from human tissue, non-human tissue, synthetic materials, and combinations of the above materials. Tissue engineered skin substitutes are made up of cells, the extracellular matrix, or a combination of cells and matrices. Cellular components include keratinocytes and other cells of the epidermis, fibroblasts and other cells of the dermis, and mesenchymal stem cells. Acellular biologically derived components include collagen, glycosaminoglycans, such as chondroitin sulfate, and other components of the extracellular matrix. Chemically synthesized polymers, such as silicone, are sometimes used as a scaffold. In some cases, an acellular matrix is combined with cells to produce the skin substitute. Skin substitutes or artificial skin substitutes described herein can be attached using the microstructures described herein.

From the practical point of view, the skin substitutes are best classified as temporary or permanent and synthetic or biological. Temporary skin substitutes provide transient physiologic wound closure, including protection from mechanical trauma, physical barrier to bacteria and creation of a moist wound environment. The permanent skin substitutes have the roles of permanently achieving wound closure, replacing the skin components and providing a higher quality skin replacement than the thin autologous skin graft.

Skin substitutes are used in the treatment of conditions like burns, traumatic wounds, pressure ulcers, diabetic ulcers, arterial ulcers or venous ulcers, where skin grafts cannot be possible. In some cases, skin substitutes are used as a permanent solution. In other cases, they can be used as a temporary measure. Some of the conditions in which temporary skin substitutes are used are on donor sites of skin grafts, or to temporarily cover wounds until skin grafting can be performed.

Depending on the source, skin substitutes can be biological or synthetic. Some of the synthetic substitutes also contain biological material and can be referred to as biosynthetic skin substitutes.

Biological skin substitutes include tissues that are obtained from biological sources. These include: 1) Skin grafts obtained from animals, known as xenografts, which are usually pigs, 2) Skin grafts obtained from donors, known as allografts, which can be either living or cadavers, 3) Amnion, which is fetal tissue from the placenta, and 4) Cultured epithelial autografts that are produced by growing skin cells obtained from a small biopsy of the patient's skin.

Synthetic or bioengineered or biosynthetic skin substitutes are artificially produced. Some of them contain skin cells while others do not. Examples of those which do not contain skin cells and are therefore classified as acellular include 1) Biobrane®, which consists of a nylon mesh and an outer layer of silastic, 2) Integra®, which consists of bovine collagen, chondroitin-6-sulphate, and a silastic membrane, 3) Matriderm® which consists of bovine type I collagen with elastin, 4) Graftjacket Tissue Matrix, which is an acellular regenerative tissue matrix from that contains collagen, elastin, and proteoglycans, and the internal matrix of the dermis that is designed to provide a scaffold for wound repair, 5) Oasis Wound Dressing, which is a tissue-engineered collagen matrix derived from the porcine small intestinal submucosa, 6) AlloDerm, an acellular dermal matrix processed from human allograft skin, 7) E-Z Derm Biosynthetic Wound Dressing (Brennen Medical, Inc., St. Paul, Minn.), a porcine-derived xenograft that has been chemically modified to provide durability and storage, 8) Integra, a bilayered matrix wound dressing composed of a porous layer of cross-linked bovine tendon collagen and glycosaminoglycan and a semipermeable polysiloxane (silicone) layer, 9) MatriStem, a unique epithelial basement membrane which is known to be composed of several types of collagen, adhesion proteins, glycoproteins, and other elements of an extracellular matrix, 10) hMatrix acellular dermis, a dermal scaffold processed from donated human skin, 11) Mediskin, a frozen irradiated porcine-derived de-cellularized fetal skin product with a dermal and epidermal layer, 12) AlloSkin RT human allograft, a meshed, biologic wound covering comprised of human cadaveric dermis, 13) MemoDerm, a sterile acellular dermal allograft derived from aseptically processed cadaveric human skin tissue that is terminally sterilized, 14) Matrix HD, a sterile dehydrated acellular dermis from donated human tissue. 15) Unite Biomatrix, a wound biomodulating decellularized extracellular matrix that is sourced from equine pericardium, 16) EndoForm Dermal Template, an extracellular matrix derived from ovine forestomach, 17) DermaSpan, an acellular dermal matrix derived from aseptically processed cadaveric human allograft skin tissue, 18) Integuply, an acellular human dermis derived from aseptically processed human allograft skin tissue, 19) DermaMatrix tissue, an allograft derived from donated human skin, which consists of acellular dermal collagen matrix, and 20) Suprathel, a synthetic, biocompatibie, and absorbable skin substitute made from polymers of lactic acid.

Cellular skin substitutes contain some types of skin cells. These include keratinocytes, which are the most common cells of the skin, and fibroblasts, which produce fibrous tissue. The cells are often obtained from the foreskin of the penis obtained from babies undergoing circumcision. Examples of cellular skin substitutes are: 1) Apligraf®, which consists of type I bovine collagen, and keratinocytes and fibroblasts form the cellular component. 2) TransCyte®, which consists of a nylon mesh and outer silastic layer, with fibroblasts as the cellular component, 3) OrCel® which consists of skin cells in two layers and type I bovine collagen sponge, 4) Hyalomatrix®, which consists of hyaluronan base, fibroblasts and an outer silicone membrane, 5) Dermagraft®, which is a bioabsorbable polyglactin mesh with fibroblast cells, 6) Orcel, an absorbable bilayered cellular matrix, made of bovine collagen, in which human dermal cells have been cultured, 7) Epicel, which is made of autologous keratinocytes obtained from the patient's skin, 8) TheraSkin, a biologically active, cryopreserved human skin allograft with both epidermis and dermis layers, 9) EpiFix, a multi-layer biologic dehydrated human amniotic membrane allograft comprised of an epithelial layer and two fibrous connective tissue layers, 10) DermACELL, regenerative human dermal allograft procured and processed from donated human tissue, 11) Grafix CORE, an allograft derived from human chorionic placental tissue that contains mesenchymal stem cells, anti-inflammatory cytokines, growth factors, and a collagen rich membrane, and 12) Laserskin, autologous keratinocytes derived from the patient's own skin.

Other treatment modalities also require attachment to the skin. For example, electrical stimulation requires attachment of the electrodes to the skin or wound area. An adhesive material can be used for this purpose which is incorporated into a dressing or to the electrode itself. Alternatively, nanogenerators use adhesive bandage material to attach to the skin or wound area. In some cases, topical oxygen is applied directly to the wound via dressings that incorporate the source of oxygen. These dressings are typically attached to the skin using adhesive. Finally, negative pressure dressing, such as the WoundVac, also require attachment of the device itself as well as the sponge that is part of the device to the skin or wound area.

Securing wound dressings and skin substitutes to underlying tissue and the patient's skin surrounding the graft can be problematic Adhesive material either incorporated into the dressings or applied as a bandage are often used to attach dressings. Adhesives often damage the skin resulting in skin tears and blisters. The surrounding skin is often fragile making it challenging to apply sutures or staples without tearing the skin. Attaching staples and sutures to skin substitutes is difficult due to their fragile nature. In addition, it is usually not possible to secure wound dressings with sutures or staples due to the materials of which they are made. Adhesive adheres poorly to moist skin, which is often present in patients with wounds. They are thus suboptimal for securing both skin substitutes and wound dressings in place. In addition, staples, sutures, and adhesives are typically used to attach die perimeter of skin substitutes and skin grafts to the wound. The inner portion of skin substitutes and skin grafts is not attached, leaving them at risk of shear and fluid exudate which can cause dislodgement and/or poor engraftment.

Consequently, there is an unmet need for devices that securely attach skin grafts, skin substitutes, and wound dressings to the patient's underlying tissue and surrounding skin. The devices and methods of the present disclosure are designed to provide a solution to this problem by providing microstructures incorporated into wound covers, wound dressings, skin substitutes, and skin replacement layers that achieve secure attachment of these devices. This allows more secure attachment of these materials over the wound, thus more effectively covering the wound, enabling wound healing and anti-microbial agents to more optimally contact the wound, and improving skin engraftment. A wound cover can be generally considered anything that covers a wound, such as a bandage, dressing, skin replacement layer (skin grafts, skin substitutes), gauze, film, backing and the like, and combinations thereof. These and other wound covers can be attached using the microstructures described herein.

The body of the devices disclosed herein, such as those that can be attached using the microstructures described herein, can include or be made of natural skin, skin substitutes, transparent films, and gauzes. In some examples the body can include a matrix. For example, the body can include a matrix comprising one or more of hydrofibers, hydrogels, hydrocolloids, exudative absorbers, collagens, and polymers including both natural and synthetic, chitosan and alginates. The bodies can be impregnated with bismuth, petroleum, silver, and carboxymethylcellulose. The bodies can include recombinant proteins, peptides, or small molecules that facilitate wound healing, prevent infection, or prevent bleeding.

The body can be made of a stretchable and breathable backing. For example, the body can be a polyurethane-based film and non-woven polyester film. In some examples, for example, the body can be made of a material that is transparent, or substantially transparent, thus allowing for non-invasive monitoring of wound healing. In other examples, the body can be made of a material that is not transparent. In some examples, bodies described herein are in the form of sheets, bandages; rolls; films; cloths; woven materials; non-woven materials, paper based materials, permeable, semi-permeable, or impermeable coverings, or any combinations of materials thereof. Bodies can be made of natural, synthetic, and/or artificial materials, and in some examples, they comprise a polymeric substance (e.g., a silicone, a polyurethane, or a polyethylene). Bodies can be comprised of materials that are nontoxic, biodegradable, bioresorbable, or biocompatible. In some examples, bodies of examples described herein comprise inert materials, and in some examples, the bodies comprise activated materials, (e.g., activated carbon cloth to remove microbes, as disclosed in WO2013028966A2, incorporated herein in its entirety). In some examples, bodies of examples described herein comprise a material singularly, or in combination, selected from the group consisting of medical tape, white cloth tape, surgical tape, tan cloth medical tape, silk surgical tape, clear tape, hypoallergenic tape, silicone, elastic silicone, polyurethane, elastic polyurethane, polyethylene, elastic polyethylene, polyester, rubber, latex, Gore-Tex, plastic and plastic components, polymers, biopolymers, and natural materials. In some examples, bodies, can include commercially available material, such as 3M Transpore Surgical Tape, 3M Blenderm Surgical Tape, Coverlet Fabric, Dynarex Silk Surgical Tape, KENDALL™ Hypoallergenic Clear Tape, TENDERFIX™ Hypoallergenic Cloth Tape, CURASILK™ Cloth Tape, Curapont, Leukosan Skinlink, Leukosan Strip, Leukostrip, Steri-Strip, Steri-Strip S, Urgo strip, and combinations thereof.

The flexibility and/or stretch ability of the body can be uniform throughout. Alternatively, the flexibility and/or stretchability of the body can vary across, or along, the device. Further, in some examples, bodies described herein can comprise elastic properties, wherein the elasticity can optionally be similar throughout the device. Alternatively, the elasticity can be varied along or across the device.

FIG. 3 shows a wound dressing or cover 300 having a body 302 that is elongated with straight sides and rounded opposing ends. The microstructure array is shown as a continuous array that is parallel to the outer perimeter 303 of the body. The array 310 includes a plurality of microstructures 104 for attachment to a tissue or other object. The microstructures are shown in four groups, two on the opposing ends and two on each side of the body 302. The microstructures can be of any form that engages with tissue or an object, such as those discussed in the '739 and '039 Publications.

The array 310 can include a plurality of spring portions, e.g., undulating portions, as discussed with reference to FIGS. 1 and 2, or cannot include such spring portions.

Figure 4:
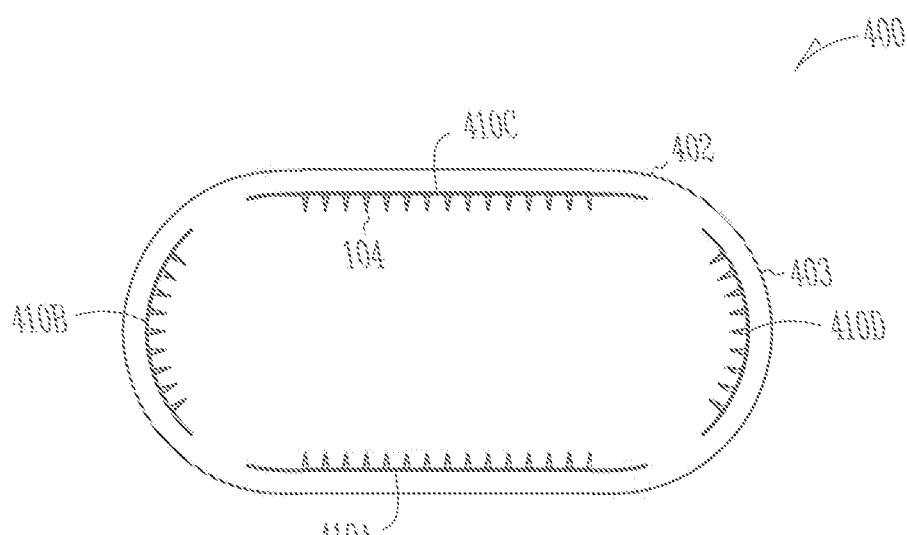
FIG. 4 illustrates a wound cover or dressing with microstructures, in accordance with one or more examples herein.

FIG. 4 shows a wound dressing or cover 400 having a body 402 that is elongated with straight sides and rounded opposing ends that is substantially similar to that shown in FIG. 3. The wound dressing or cover 400 includes a plurality of microstructure arrays 410A, 410B, 410C, 410D. Each microstructure array 410 includes a plurality of microstructures 104 for attachment to a tissue or other object. Each array 410 follows the contours of the outer perimeter 403 of the body 402. The microstructures arrays are arranged in four locations about the body 402, two arrays 410B, 410D are located at the opposing ends and two arrays 410A, 410C are located on each side of the body 302. The microstructures can be of any form that engages with tissue or an object, such as those discussed in the '739 and '039 Publications.

The arrays 410 can include a plurality of spring portions, e.g., undulating portions, as discussed with reference to FIGS. 1 and 2, or can not include such spring portions.

Figure 5:
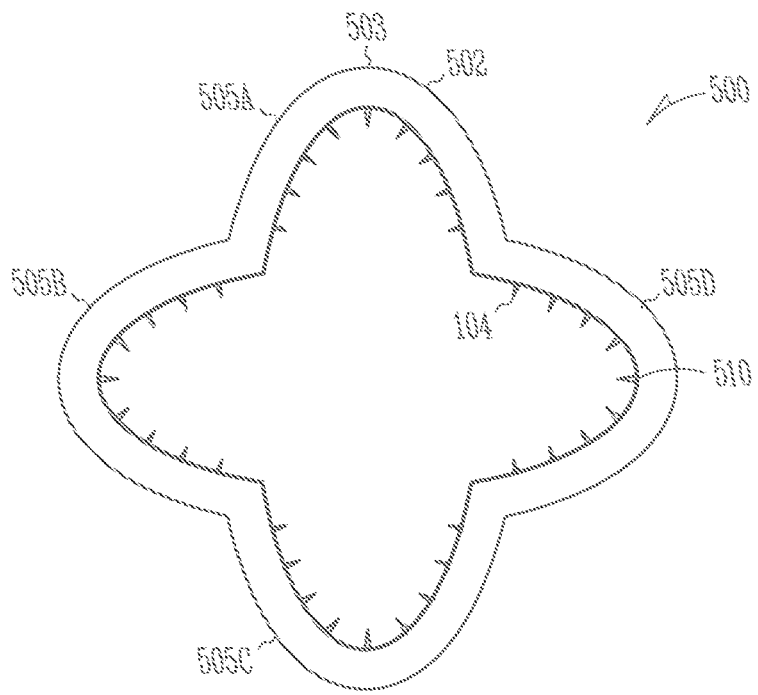
FIG. 5 illustrates a wound cover or dressing with microstructures, in accordance with one or more examples herein.

FIG. 5 shows a wound dressing or cover 500 having a body 502 that has a central portion and four elongated lobes 505A, 505B, 505C, 505D that extend from the central portion of the body 502. The microstructure array is shown as a continuous array that is parallel to the outer perimeter 503 of the body. The wound dressing or cover 500 includes a microstructure array 510 that includes a plurality of microstructures 104 for attachment to a tissue or other object. The microstructures are shown in four groups, one group for each lobe 505 of the body 502. As with the arrays in FIGS. 3 and 4, the array 510 follows the perimeter 503 of the body 502. The microstructures 104 can be of any form that engages with tissue or an object, such as those discussed in the '739 and '039 Publications.

The array 510 can include a plurality of spring portions, e.g, undulating portions, as discussed with reference to FIGS. 1 and 2, or can not include such spring portions.

Figure 6:
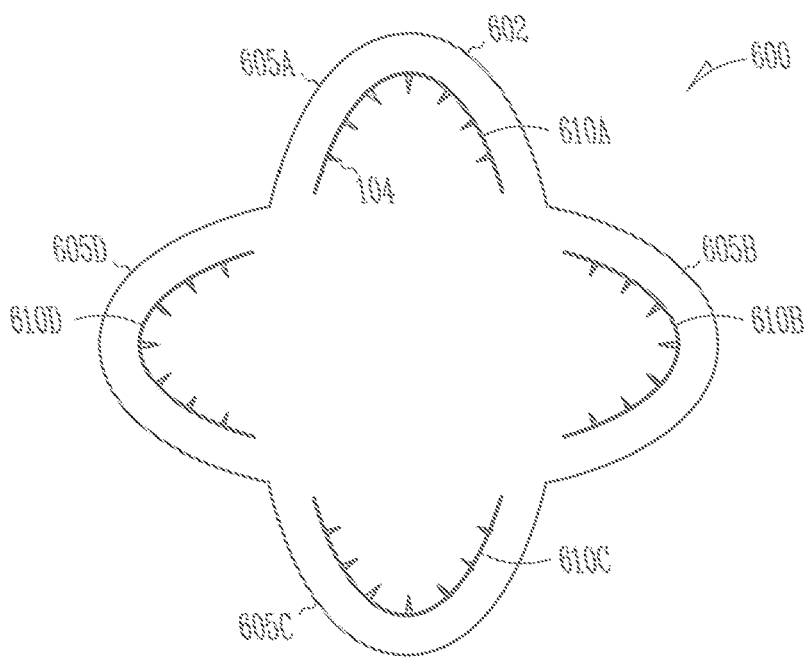
FIG. 6 illustrates a wound cover or dressing with microstructures, in accordance with one or more examples herein.

FIG. 6 shows a wound dressing or cover 600 having a body 602 that has a central portion and four elongated lobes 605A, 605B, 605C, 605D that extend from the central portion of the body 602 and is substantially similar to that shown in FIG. 5. The wound dressing or cover 600 includes a plurality of microstructure arrays 610A, 610B, 610C, 610D, one at each respective lobe 605A, 605B, 605C, 605D. Each microstructure array 610 includes a plurality of microstructures 104 for attachment to a tissue or other object. Each array 610 follows the contours of the outer perimeter 603 each respective lobe 605 of the body 602. The microstructures can be of any form that engages with tissue or an object, such as those discussed in the '739 and '039 Publications.

The arrays 610 can include a plurality of spring portions, e.g., undulating portions, as discussed with reference to FIGS. 1 and 2, or cannot include such spring portions.

Figure 7:
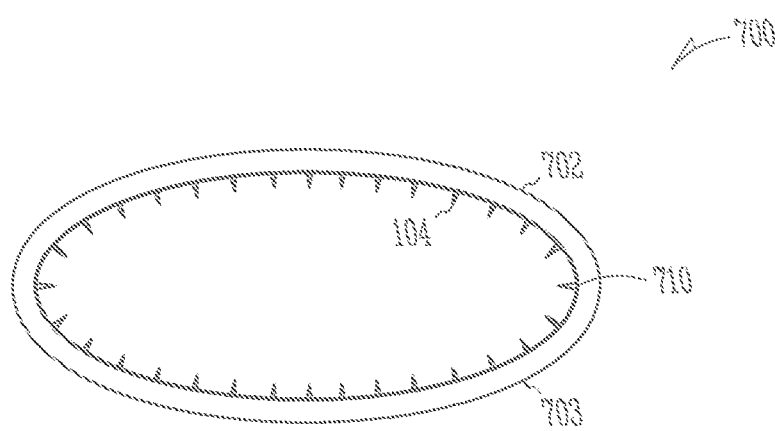
FIG. 7 illustrates a wound cover or dressing with microstructures, in accordance with one or more examples herein.

FIG. 7 shows a non-limiting example of a wound cover or dressing 700 having a body 702. The body 702 that is oval shaped. The wound cover or dressing 700 also includes a microstructure array 710 of microstructures 104. The microstructures can be coupled or otherwise attached to the body 702 of the wound cover or dressing 700. The microstructures engage a tissue or other object to couple the wound cover or dressing 700 to the object.

As shown in FIG. 7, the microstructure array is a continuous, oval array of microstructures 104. The microstructures 104 can be of any form that engages with tissue or an object, such as those discussed in the '739 and '039 Publications. The microstructure array can also include spring portions, such as those discussed in the '739 and '039 Publications.

The microstructure array 710 can include a staggered arrangement of microstructures. For example, the array can include inner microstructures located more towards the center of the body 702 of the wound cover or dressing 700 and outer microstructures located more towards the outer perimeter 703 of the body 702 of the wound cover or dressing 700.

Figure 8:
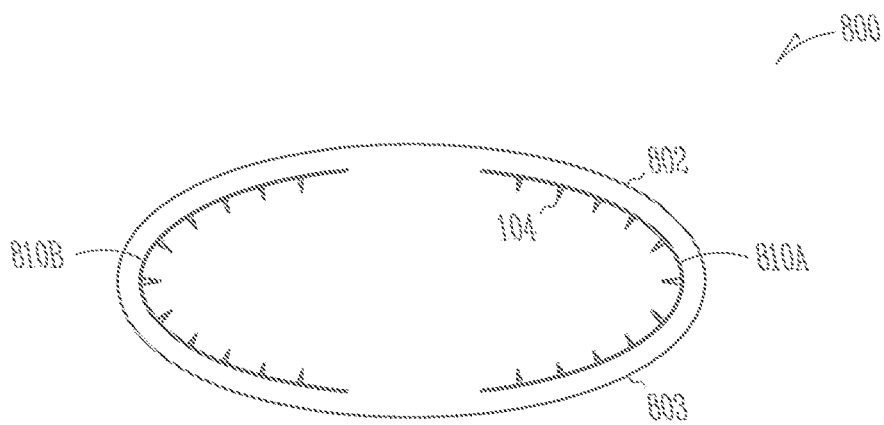
FIG. 8 illustrates a wound cover or dressing with microstructures, in accordance with one or more examples herein.

FIG. 8 shows a non-limiting example of a wound cover or dressing 800 having a body 802. The body 802 that is oval shaped. The wound cover or dressing 800 also includes a plurality of microstructure arrays 810 of microstructures 104. The microstructures can be coupled or otherwise attached to the body 802 of the wound cover or dressing 800. The microstructures engage a tissue or other object to couple the wound cover or dressing 800 to the object.

As shown in FIG. 8, the microstructure arrays 810a, 810b are located at opposite ends of the major axis of the oval shaped body 802. The microstructures 104 can be of any form that engages with tissue or an object, such as those discussed in the '739 and '039 Publications. The microstructure array can also include spring portions, such as those discussed in the '739 and '039 Publications.

The microstructure arrays 810 can include a staggered arrangement of microstructures. For example, the array can include inner microstructures located more towards the center of the body 802 of the wound cover or dressing 800 and outer microstructures located more towards the outer perimeter 803 of the body 802 of the wound cover or dressing 800.

Figure 9:
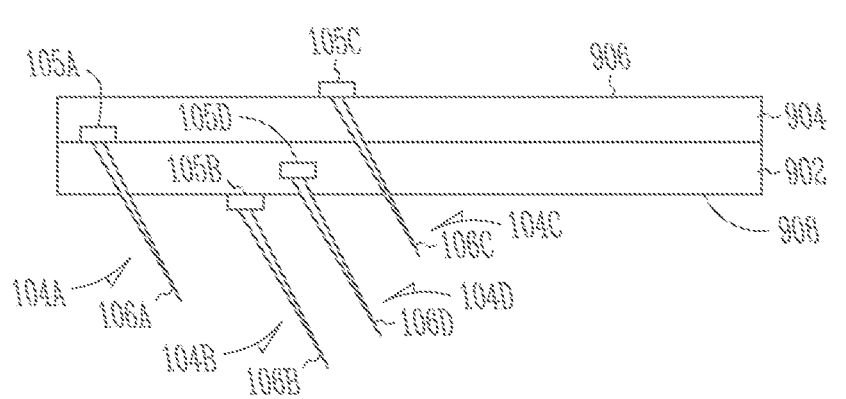
FIG. 9 illustrates cross section of a wound cover or dressing with microstructures, in accordance with one or more examples herein.

FIG. 9 illustrates a cross section of wound cover or dressing 900 which can represent a cross section of a portion of any of the wound cover or dresses discussed herein. Dressings can have one or more layers, sometime referred to a single- or multi-ply construction. The dressing or cover 900 includes a top surface 906 that faces away from the wound and a bottom surface 908 that faces the wound. The dressing or cover 900 is a two-ply construction having a first layer or ply 904 that is away from the wound and a second layer or ply 902 that is near the wound. Layers 902 and 904 can comprise any of the "bodies" described herein. FIG. 9 further illustrates several options for the arrangement of microstructures 104. Microstructure 104A includes a base portion 105A that is located between the first layer 904 and the second layer 902 and includes a shaft 106A that extends through the second layer and the bottom surface 908. Microstructure 104B includes a base portion 105B that is located at the bottom surface 908 of the dressing or cover 900 and includes a shaft 106B that extends from the base 105B away from the dressing or cover 900, without passing through any of the plays or layers of the dressing or cover 900. Microstructure 104C includes a base portion 105C that is located at the top surface 906 and includes a shaft 106C that extends through the top surface 906, the first layer 904, the second layer 902, and the bottom surface 908. Microstructure 104D includes a base portion 105D that is located within a layer, for example, the second layer 902, and includes a shaft 106D that extends through a portion of the second layer 902 and the bottom surface 908. Microstructures 104A-104D can be incorporated into any of the devices described herein, such as those of FIGS. 1-8, where microstructures 104A-104D can comprise microstructures 104 and base portions 105A-105D can comprise a body, wire or spring connecting microstructures 104.

Figure 10:
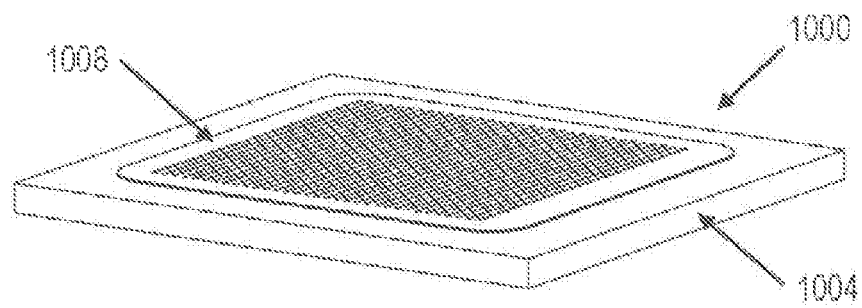
FIG. 10 illustrates a perspective view of a wound cover device incorporating a skin replacement layer attached to an exterior of skin via a micro-staple array.
Figure 11:
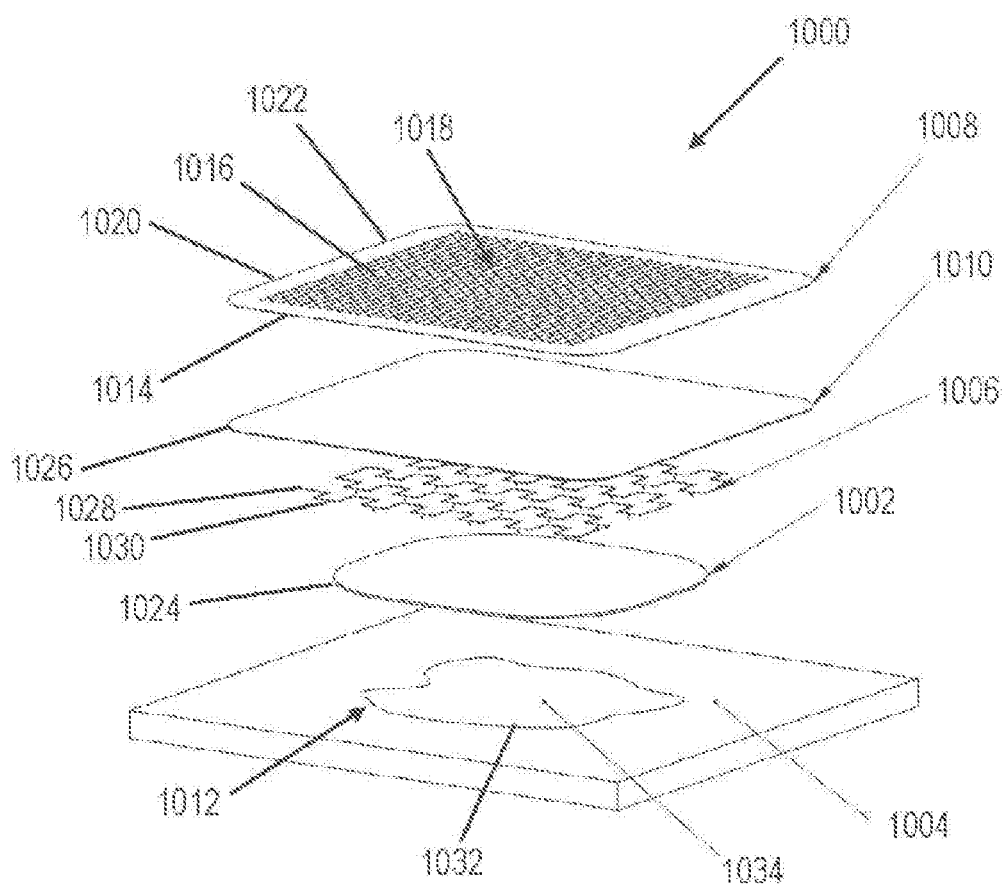
FIG. 11 illustrates an exploded view of the wound cover device of FIG. 10 showing a skin replacement layer, a micro-staple array, an adhesive layer and a hacking positioned over a portion of skin having a wound.
Figure 12:
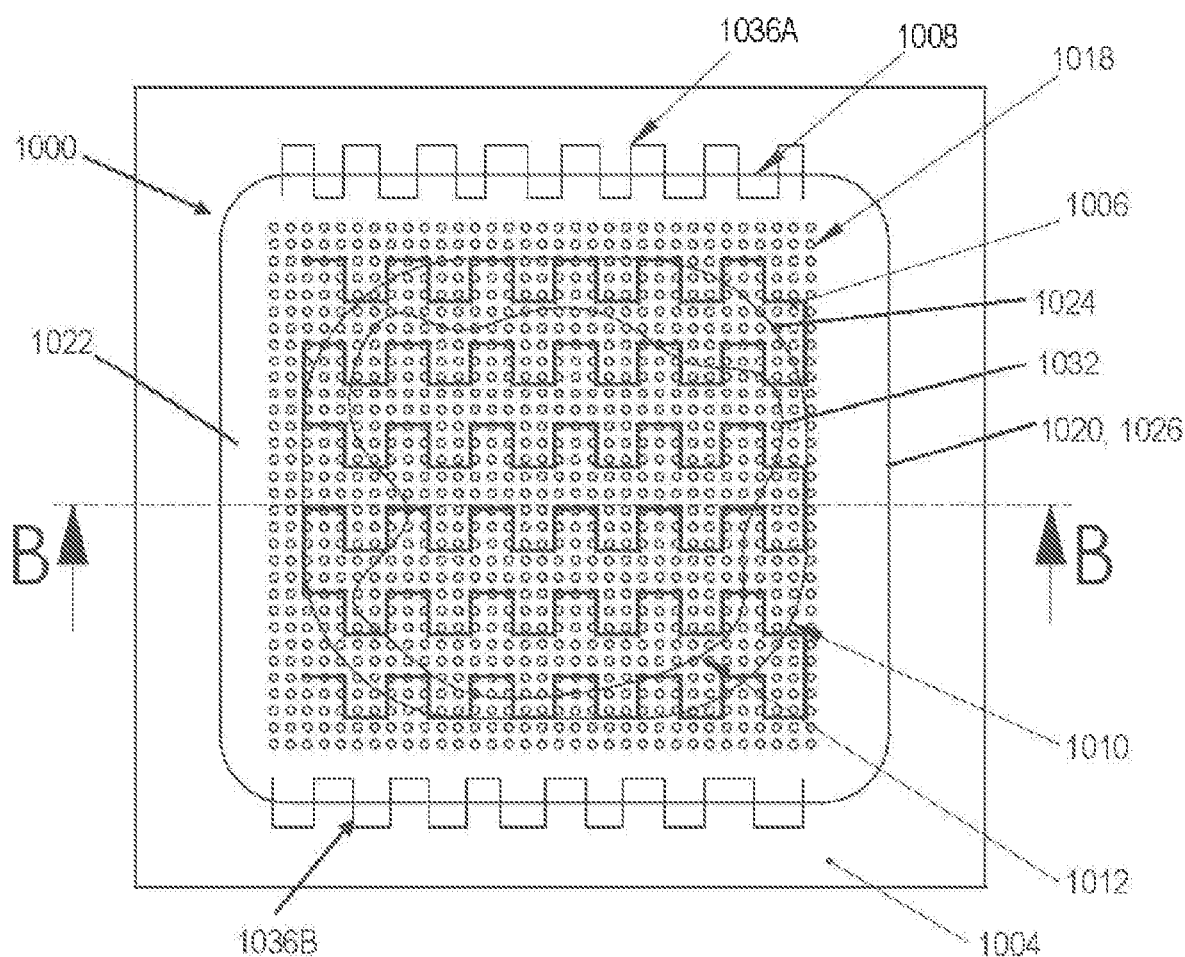
FIG. 12 illustrates a top view of the wound cover device of FIGS. 10 and 11 showing the positioning of the skin replacement layer, the micro-staple array and perforations in the backing relative to the wound in the skin.

FIG. 10 illustrates a perspective view of wound cover device 1000 incorporating skin replacement layer 1002 attached to exterior of skin 1004 via a microstructure array, such as micro-staple array 1006, which is visible in FIGS. 11 and 12. Wound cover device 1000 can further comprise backing 1008, which can be coupled to micro-staple array 1006 via adhesive layer 1010. Skin 1004 can include wound 1012 FIG. 11 illustrates an exploded view of wound cover device 1000 of FIG. 10 showing skin replacement layer 1002, micro-staple array 1006, adhesive layer 1010 and backing 1008 positioned over a portion of skin 1004 having wound 1012. FIGS. 10 and 11 are discussed concurrently.

Backing 1008 can comprise wound-side surface 1014, exterior-side surface 1016, perforation array 1018, perimeter 1020 and border 1022. Skin replacement layer 1002 can comprise perimeter 1024. Adhesive layer 1010 can comprise perimeter 1026. Micro-staple array 1006 can comprise band 1028 and barbs or staples 1030. Wound 1010 can comprise perimeter 1032 and interior 1034. As shown in FIG. 12, wound cover device 1000 can further comprise edge micro-staple arrays 1036A and 1036B.

Wound cover device 1000 is configured to hold skin replacement layer 1002 against wound 1012. In particular, micro-staple array 1006 can be configured to hold skin replacement layer 1002 against interior 1034 such that skin replacement layer 1002 is better able to facilitate healing of wound 1010, such as by promoting engraftment of skin replacement layer 1002 with skin 1004. Furthermore, micro-staple array 1006 can be configured to stretch in multiple directions to maintain skin replacement layer 1002 in engagement with wound 1010 and avert irritation to the patient from wound cover device 1000. In various examples, wound cover device 1000 can be configured to include a bandage or dressing in addition or as an alternative to skin replacement layer 1002. For example, a bandage or dressing layer can be added between backing 1008 and skin replacement layer 1002, such that staples of micro-staple array 1006 can extend through both of the bandage or dressing and skin replacement layer 1002.

Skin replacement layer 1002 can be configured to cover and fill-in interior 1034 of wound 1012. Skin replacement layer 1002 can comprise human skin, such as from the patient of skin 1004 or from a donor, synthetic skin, or animal skin, such as from a pig. As explained herein, skin replacement layer 1002 can comprise: skin grafts obtained from animals, known as xenografts, which are usually pigs, 2) skin grafts obtained from donors, known as allografts, which can be either living or cadavers, 3) amnion, which is fetal tissue from the placenta, and 4) cultured epithelial autografts that are produced by growing skin cells obtained from a small biopsy of the patient's skin. Other types of skin substitutes or replacements or other types of materials that promote skin generation or regeneration can be used.

Skin replacement layer 1002 can be sized to cover wound 1012. For example, skin replacement layer 1002 can be configured or selected such that perimeter 1024 is larger, equal size or smaller than perimeter 1032 of wound 1010. Skin replacement layer 1002 can be smaller than or equal size to backing 1008. If skin replacement layer 1002 is smaller than 1008, a band of backing 1008 forming border 1022 can extend beyond skin replacement layer 1002 to enable adhesive layer 1010 to attach to skin 1004. Border 1022 is an optional feature. In such configurations, adhesive layer 1010 can attach to skin 1004 away from perimeter 1032 of wound 1012 where the health of skin 1004 can be improved and more resilient. In other examples, skin replacement layer 1002 can be sized to fit within perimeter 1032 of wound 1012. As discussed below, various configurations of wound cover device 1000 can be implemented to provide coverage for different sizes, shapes and depths of wounds. Depending on the application, wound cover device 1000 can also be cut to the size required for optimal fit and conformance over surrounding skin.

Backing 1008 can comprise wound-side surface 1014, exterior-side surface 1016, perforation array 1018, perimeter 1020 and border 1022. Backing 1008 can comprise any suitable material for holding micro-staple array 1006. In various examples, backing 1008 can be stretchable so as to facilitate moving and stretching with skin 1004. In examples, backing 1008 can be made of polyurethane, polyethylene or polyethylene terephthalate, polyester nonwoven, or any medical tape materials. Although, other polymer or plastic materials or other synthetic or natural materials can be used.

Adhesive layer 1010 can be any suitable material to couple micro-staple array 1006 to backing 1008 and, as such, cannot need to be adhesive, but could comprise glue or another bonding agent. Adhesive layer 1010 can comprise acrylate, including methacrylates and epoxy diacrylates (which are also known as vinyl resins), hydrocolloid, silicone, a combination thereof, sometimes known as hybrids, or any known medical adhesive materials. In examples, adhesive layer 1010 can flex and stretch with backing 1008. Adhesive layer 1010 can, in examples, cover all or substantially all of wound-side surface 1014 of backing 1008.

FIG. 12 illustrates a top view of wound cover device 1000 of FIGS. 10 and 11 showing the positioning of skin replacement layer 1002, micro-staple array 1006 and perforations 1018 in backing 1008 relative to wound 1012 in skin 1004. Additionally, edge micro-staple arrays 1036A and 1036B can be attached to backing 1008 as an optional feature to facilitate joining of wound cover device 1000 to skin 1004, such as away from skin replacement layer 1002. Edge micro-staple arrays 1036A and 1036B can provide additional securement of wound cover device 1000 to skin 1004, such as away from wound 1012 at the edges of backing 1008 where peeling or crumpling can occur 1036A and 1036B can be used with or without the existence of micro-staple array 1006 in wound cover device 100.

Wound cover device 1000 can be configured in a variety of different sizes. That is, a manufacturer of wound cover device 1000 can produce devices of similar layers and components as wound cover device 1000, but that are configured to cover wounds of different sizes, shapes and depths. As such, wound cover device 1000 can be configured in different sizes and shapes, such as squares, rectangles, circles and other shapes. Likewise, the size and shape of skin replacement layer 1002 can be varied to accommodate different wounds, and the thickness of skin replacement layer 1002 can be varied to accommodate wounds of different thicknesses. In examples, skin replacement layer 1002 can have varying thickness within a single device. In other examples, skin replacement layer 1002 can be configured to cover only a portion or extended beyond the perimeter of micro-staple array 1006.

As can be seen in FIG. 12, a configuration of wound cover device 1000 can be selected to so that skin replacement layer 1002 completely covers wound 1012. Thus, perimeter 1024 and the surface area within perimeter 1024 can be larger than perimeter 1032 and the surface area within perimeter 1032. However, in various examples, skin replacement layer 1002 can be larger than, equal to or smaller than wound 1012. Backing 1008 can be larger than skin replacement layer 1002. Thus, perimeter 1020 and the surface area within perimeter 1020 can be larger than perimeter 1024 and the surface area within perimeter 1024. Adhesive layer 1010 can be the same size as backing 1008 or can be positioned only along a perimeter region enough for attaching micro-staple array 1006 and skin replacement layer 1002, and at selected local areas within perimeter 1020, such as at border 1022. Thus, perimeter 1026 can be the same size as perimeter 1020. As such, a width of backing 1008 forming border 1022 can surround skin replacement layer 1002, thereby permitting adhesive layer 1010 to directly contact skin 1004 at healthy portions thereof away from wound 1012. In other examples, adhesive layer 1010 can be sized to only provide coupling of micro-staple array 1006 to backing 1008 such that micro-staple array 1006 provides the only coupling of wound clover device 1000 to skin 1004. For example, adhesive layer 1010 can be sized to not over border 1022 of backing 1008.

In other examples, skin replacement layer 1002 can be the same size as backing 1008 and adhesive layer 1010 such that perimeters 1020, 1024 and 1026 are the same size to, for example, facilitate manufacturing.

As can be seen in FIG. 12, perforations 1018 can be provided in backing 1008. Perforations 1018 can comprise a plurality of holes extending through backing 1008 from wound-side surface 1014 to exterior-side surface 1016. Perforations 1018 can facilitate drainage and breathing of wound 1012. Perforations 1018 need not extend all the way to perimeter 1020 of backing 1008 in order to, for example, facilitate good adhesion of backing 1008 to skin 1004 via adhesive layer 1010. For example, border 1022 or other selected areas can be free of perforations 1018. However, in other examples, perforations 1018 can extend to perimeter 1020 to, for example, facilitate manufacturing. Perforations 1018 can be arranged in an array or pattern on backing 1008. In the example shown, perforations 1018 are arranged in a grid structure of rows and columns of circular holes having the same diameter and the same spacing. However, perforations 1018 can be arranged in other configurations and densities and have other shapes and sizes. Perforations 1018 can include holes of varied sizes and can be spaced non-uniformly. Perforations 1018 can be configured to cover a percentage of the surface area of wound 1012. For example, the holes defining perforations 1018 can be configured to cover a percentage of interior 1034. In an example, perforations 1018 can cover from approximately 0.1 percent to approximately seventy-five percent of interior 1034. In a particular example, perforations 1018 cover approximately fifty percent of interior 1034. Perforations 1018 are only approximately circular and can also be oval depending on the manufacturing method used. However, other shapes can also be used. Furthermore, the perforation density can also vary throughout the device.

Micro-staple array 1006 can comprise any type of microstructure or micro-staple described herein. Micro-staple array 1006 can comprise band 1028 and staples 1030. Band 1028 can comprise, for example, a shaped metal wire, or a stamped or etched ribbon. In the depicted example, band 1028 is arranged to have macro and micro serpentine patterns. For example, in one particular example, band 1028 is wound to make six horizontal lengths across backing 1008 with five short vertical lengths connecting the horizontal lengths on alternating sides, with regard to the specific orientation of FIG. 12. Each horizontal length can have to itself approximately six square-wave patterns. Such a configuration can provide micro-staple array 1006 with stretchability in the vertical and horizontal directions. In other examples, micro-staple array 1006 can have other micro and macro patterns to, for example, provide stretching capabilities in one or more directions. For example, arrays 110, 210, 310, 410, 510, 610, 710 and 810 of FIGS. 1-8 can be incorporated into various configurations of wound cover device 1000. In various examples, micro-staple array 1006 can comprise other microstructures such as cantilevered springs, including those discussed in the '739 and '039 Publications. The number and spacing of staples 1030 along band 1028 can vary in different examples. In examples, each square-wave segment can have a microstructure such as one of staples 1030. In additional examples, only the horizontal or vertical square-wave segments can have a microstructure to facilitate directional stretching.

Micro-staple array 1006 can have vertical and horizontal dimensions that approximately equal those dimensions of skin replacement layer 1002. As such, perimeter 1024 of skin replacement layer 1002 and the interior of skin replacement layer 1002 within perimeter 1024 can be attached to wound 1012 using staples 1030. As such, perimeter 1032 and interior 1034 of wound 1012 can additionally be covered with portions of skin replacement layer 1002 held in place with staples 1030. In examples, micro-staple array 1006 can be provided in a plurality of sub-sections that are separate from each other, but that can be distributed across backing 1008 to provide coverage of skin replacement layer 1002. Thai is, for example, micro-staple array 1006 can be formed by four smaller square-shaped devices that are separated from each other, but that provide the same coverage as micro-staple array 1006.

Edge micro-staple arrays 1036A and 1036B can additionally be provided on backing 1008 to provide improved securement around the perimeter of backing 1008. FIG. 12 depicts two edge micro-staple arrays, but fewer or greater numbers of edge micro-staple arrays can be used. For example, four edge micro-staple arrays could be included with the illustrated example of wound cover device 1000 along each of the four edges of backing 1008. Edge micro-staple arrays 1036A and 1036B can be configured as single serpentine lengths of wire extending along perimeter 1020 of backing 1008 in a square-wave pattern. However, edge micro-staple arrays of any shape and size can be used, such as those shown and described with reference to FIGS. 1-9. Edge micro-staple arrays used with wound cover device 1000 can be configured to follow the contour of perimeter 1020 of backing 1008.

In additional examples, wound cover device 1000 can be configured to be cut or torn to different sizes. For example, backing 1008 and skin replacement layer 1002 can be provided with perforations to facilitate ripping or tearing. Micro-staple array 1006 can be provided in a plurality of sub-sections corresponding to each sub-section of backing 1008 and skin replacement layer 1002 formed by perforations or other indicators or borders within wound cover device. In other configurations, micro-staple array 1006 can be configured to be sliced or cut by a knife or scissors, such as at band 1028.

Figure 13:
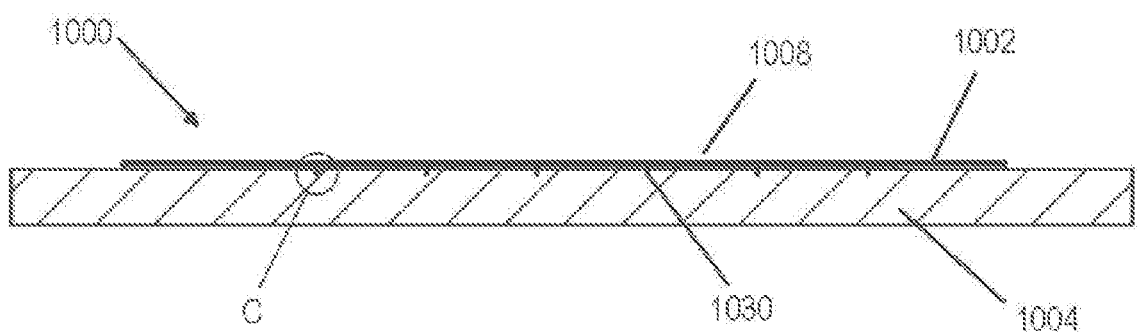
FIG. 13 illustrates a cross-sectional view of the wound cover device of FIG. 12 taken at section B-B to show staples of the micro-staple array holding the wound cover device to the skin.
Figure 14:
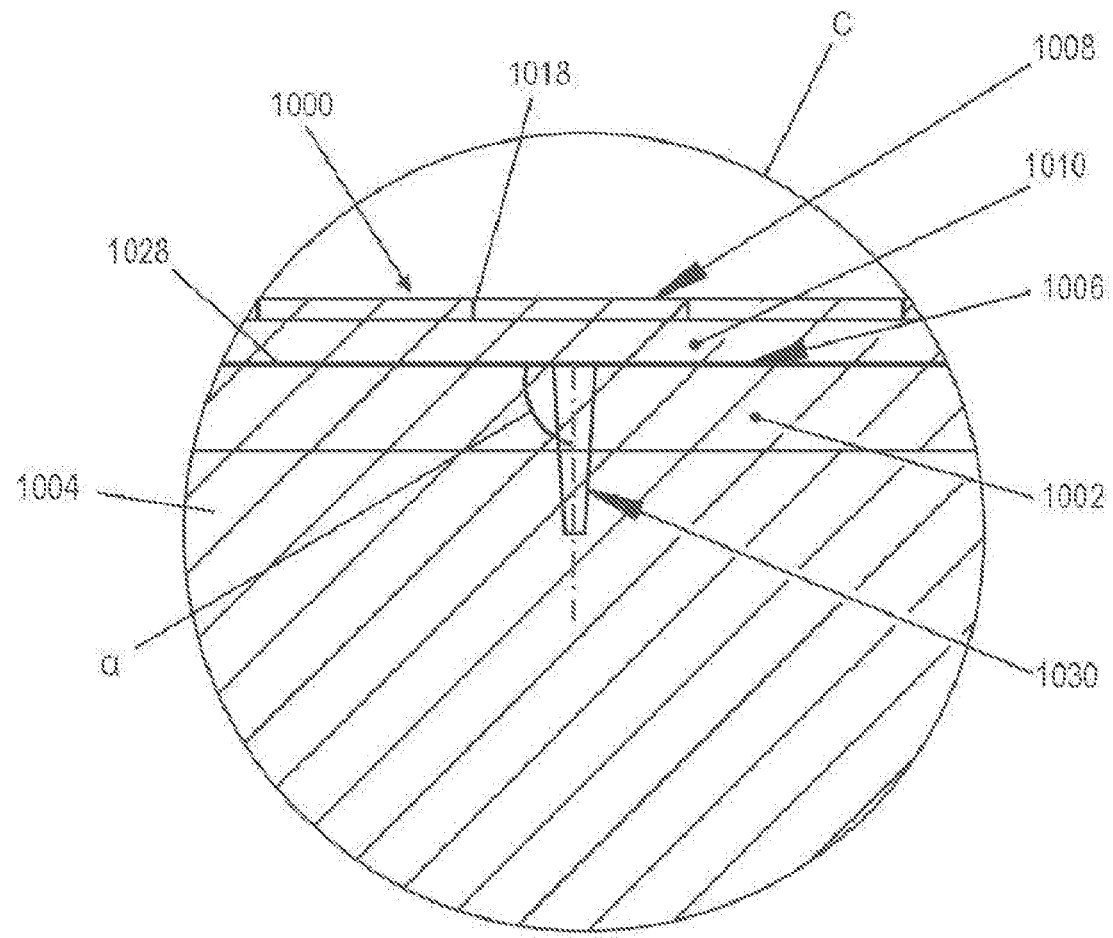
FIG. 14 is a close-up view of callout A of FIG. 13 showing a staple of the micro-staple array extending from the adhesive layer on the backing to extend through the skin replacement layer and into the skin.

FIG. 13 illustrates a cross-sectional view of wound cover device 1000 of FIG. 12 taken at second B-B to show staples 1030 of micro-staple array 1006 holding wound cover device 1000 to skin 1004. FIG. 14 is a close-up view of callout C of FIG. 13 showing staple 1030 of micro-staple array 1006 extending from band 1028, which is held against adhesive layer 1010 on backing 1008, to extend through skin replacement layer 1002 and into skin 1004. FIGS. 13 and 14 are discussed concurrently. A selected quantity of staples 1030 can be made shorter than others of staples 1030 to be used for securement of skin replacement layer 1002 only, e.g., such shorter of staples 1030 will not be used to anchor to tissue. In such examples, the spacing between the longer of staples 1030 that are inserted into tissue can be increased/altered for optimal treatment.

Micro-staple array 1006 can be held to backing 1008 via adhesive layer 1010. In particular, band 1028 can be held in close proximity to wound-side surface 1014 of backing 1008 via adhesive layer 1010. Staples 1030 can be formed integrally with band 1028, such as via an etching or stamping process, or can be attached via various manufacturing methods. Each of staples 1030 can extend away from wound-side surface 1014 toward and into or through skin replacement layer 1002. For anchoring, each of staples 1030 can have a length sufficient to extend through skin replacement layer 1002 and penetrate into skin 1004. In various examples, staples 1030 can have a length in the range of approximately 0.5 mm to approximately 10 mm. In various examples, staples 1030 can be sized according to the thickness of skin replacement layer 1002. In various examples, it can be desirable to have each of staples 1030 extend into skin 1004 to a depth of at least 0.5 mm. However, as discussed above, at least some of staples 1030 can be configured not to extend into skin 1004 and can be used only for fastening to skin replacement layer 1002.

Each or some of staples 1030 can be configured to penetrate into skin 1004 to anchor wound cover device 1000. For example, each of staples 1030 can be of any form that engages with tissue or an object, such as those discussed in the '739 and '039 Publications. In the depicted example, each staple 1030 comprises an isosceles trapezoid shape, with the shortest edge being positioned furthest away from backing 1008 and the longest, non-parallel sides extending along a major axis generally perpendicular to backing 1008. In other examples, staples 1030 can come to a sharp point. In examples, a proximal portion of staples 103 near backing 1008 can include attachment features, such as barbs, for securing skin replacement layer 1002, while portions of staples 1030 that penetrate through skin replacement layer 1002 can be free of the attachment features so as to not disturb or damage tissue.

The major axis of staples 1030 can extend from backing 1008 at angle α. In various examples, angle α can be in the range of forty-five to ninety degrees. In examples, all of staples 1030 can have the same angle α. However, in other examples, staples 1030 can have varying angles α in a single device.

While preferred examples of the present invention have been shown and described herein, it will be obvious to those skilled in the art that such examples are provided by way of example only. Numerous variations, changes, and substitutions will now occur to those skilled in the art without departing from the invention. It should be understood that various alternatives to the examples of the invention described herein can be employed in practicing the invention. It is intended that the following claims define the scope of the invention and that methods and structures within the scope of these claims and their equivalents be covered thereby.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with requirements, to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. The scope of the invention should be determined with reference to the appended claims, along with the full scope of equivalents to which such claims are entitled.

The invention claimed is:

1. A wound cover device comprising:
a backing comprising a wound-side surface and an exterior-side surface;
one or more micro-staple arrays attached to the wound-side surface, wherein the one or more micro-staple arrays comprise a base wire extending in a repeating undulating pattern and a plurality of staples extending from repeating positions along the base wire, and
a wound treatment layer attached to the one or more micro-staple arrays,
wherein the base wire can include an outer perimeter larger than an outer perimeter of the wound treatment layer, and
wherein the one or more micro-staple arrays comprises a matrix of evenly distributed staples that uniformly distributes staples across an interior of the wound treatment layer.

2. The wound cover device of claim 1, wherein the wound treatment layer comprises a skin replacement layer comprising natural skin, synthetic skin or a combination thereof.

3. The wound cover device of claim 2, wherein the wound treatment layer comprises a skin replacement layer comprising a xenograft, an allograft, an autograft or a combination thereof.

4. The wound cover device of claim 2, wherein the backing comprises polyurethane, polyethylene or polyethylene terephthalate.

5. The wound cover device of claim 1, wherein the backing comprises a stretchable material.

6. The wound cover device of claim 1, wherein the backing includes a perforation.

7. The wound cover device of claim 6, wherein the perforation comprises an array of holes extending through the backing from the wound-side surface to the exterior-side surface.

8. The wound cover device of claim 7, wherein the wound treatment layer is located within an outer perimeter of the array of holes.

9. The wound cover device of claim 7, wherein the array of holes is surrounded by an unbroken border of material of the backing.

10. The wound cover device of claim 1, wherein the one or more micro-staple arrays is attached to the backing with an adhesive layer.

11. The wound cover device of claim 10, wherein the adhesive layer is perforated.

12. The wound cover device of claim 10, wherein the adhesive layer comprises acrylate or other known medical adhesive materials.

13. The wound cover device of claim 10, wherein the adhesive layer completely covers the wound-facing side.

14. The wound cover device of claim 1, wherein the one or more micro-staple arrays is stretchable.

15. The wound cover device of claim 14, wherein the one or more micro-staple arrays is stretchable in orthogonal directions.

16. The wound cover device of claim 14, wherein the one or more micro-staple arrays comprises a spring structure.

17. The wound cover device of claim 1, wherein the base wire extending in the repeating undulating pattern forms a repeating square-wave pattern.

18. The wound cover device of claim 1, wherein the one or more micro-staple arrays extends across an interior of the wound treatment layer from a first edge to a second opposite edge.

19. The wound cover device of claim 1, wherein the one or more micro-staple arrays includes a plurality of staples projecting through the wound treatment layer and configured to engage the skin and anchor the wound cover device thereto.

20. The wound cover device of claim 19, wherein each of the plurality of staples has a length of at least 1 mm.

21. The wound cover device of claim 20, wherein each of the plurality of staples has a length less than or equal to 10 mm.

22. The wound cover device of claim 19, wherein at least some of the plurality of staples are angled relative to the backing at an angle in the range of ninety to forty-five degrees.

23. The wound cover device of claim 1, further comprising an edge micro-staple array disposed along and extending partially beyond an edge of the backing separate from the one or more micro-staple arrays.

24. The wound cover device of claim 1, wherein the wound treatment layer comprises a wound dressing layer.

25. The wound cover device of claim 24, wherein the wound dressing layer comprises a bandage, gauze, a cotton layer or a lint layer.

26. The wound cover device of claim 24, wherein the wound dressing layer comprises a hydrocolloid or a hydrogel.

27. A wound treatment device comprising:
a backing including a wound-side surface and an exterior-side surface;
a matrix of evenly distributed micro-staples attached to the wound-side surface;
a base wire extending in a repeating undulating pattern with the matrix of evenly distributed micro-staples extending from repeating positions along the base wire; and
a wound treatment layer including the micro-staples uniformly distributed across an interior of the wound treatment layer,
wherein the base wire can include an outer perimeter larger than an outer perimeter of the wound treatment layer.

28. A device comprising:
a backing including a wound-side surface and an exterior-side surface;
a base wire extending in a repeating undulating pattern with a matrix of evenly distributed micro-staples extending from the base wire in repeating positions; and
a wound treatment layer including the micro-staples uniformly distributed across an interior of the wound treatment layer,
wherein the base wire can include an outer perimeter larger than an outer perimeter of the wound treatment layer.

* * * * *